United States Patent [19]

Benjamin et al.

[11] Patent Number: 5,554,529
[45] Date of Patent: Sep. 10, 1996

[54] CELL LINES AND METHODS FOR ASSAYING HUMAN INTERCHROMOSOMAL RECOMBINATION

[75] Inventors: Mark B. Benjamin, Boston; John B. Little, Brookline, both of Mass.

[73] Assignee: President and Fellows of Harvard College, Cambridge, Mass.

[21] Appl. No.: 239,924

[22] Filed: May 9, 1994

Related U.S. Application Data

[63] Continuation of Ser. No. 738,316, Jul. 31, 1991, abandoned.
[51] Int. Cl.$^6$ .............................. C12N 5/08; C12N 15/01; C12N 15/54; C12N 15/11
[52] U.S. Cl. .................. 435/240.2; 435/6; 435/172.1; 435/172.3; 935/77
[58] Field of Search ................. 435/240.2, 6, 172.1, 435/172.3; 935/77

[56] References Cited

U.S. PATENT DOCUMENTS 4,792,520 12/1988 Stambrook et al. ..................... 435/6

OTHER PUBLICATIONS

Flemington, Erik et al. "Sequence Structure And Promoter Characterization Of The Human Thymidine Kinase Gene", *Gene*, 52, pp. 267–277, 1987.

Ames, B. N. et al., "Methods For Detecting Carcinogens And Mutagens With The Salmonella/Mammalian–Microsome Mutagenicity Test" *Mutation Research*, vol. 31, pp. 347–364, 1975.

Amundson, S. A. et al., "RFLP mapping of thymidine kinase mutants places D17S4 proximal to the human TK1 locus" *Nucleic Acids Research*, vol. 19, No. 13, p. 3748, 11 Jul. 1991.

Benjamin, M. B. and J. B. Little, "X Rays Induce Interallelic Homologous Recombination at the Human Thymidine Kinase Gene" *Molecular and Cellular Biology*, vol. 12, pp. 2730–2738, Jun. 1992.

Benjamin, M. B. et al., "A system for assaying homologous recombination at the endogenous human thymidine kinase gene" *Proc. Natl. Acad. Sci. USA*, vol. 88, No. 15, pp. 6652–6656, Aug. 1991.

Bhattacharyya, N. P. et al, "Intrachromosomal homologous recombination in human cells which differ in nucleotide excision–repair capacity" *Mutation Research*, vol. 234, pp. 31–41, 1990.

Cohen, A. and A. Laban, "Plasmidic Recombination in *Escherichia coli* K–12: The Role of recF Gene Function" *Mol. Gen. Genet.*, vol. 189, pp. 471–474, 1983.

Fishel, R. A. and R. Kolodner, "*Escherichia coli*, Strains Containing Mutations in the Structural Gene for Topoisomerase I Are Recombination Deficient" *Journal of Bacteriology*, vol. 160, No. 3, pp. 1168–1170, Dec. 1984.

Groden, J. et al., "Molecular evidence that homologous recombination occurs in proliferating human somatic cells" *Proc. Natl. Acad. Sci. USA*, vol. 87, pp. 4315–4319, Jun. 1990.

Kieser, H. M. et al., "A mutation of *Streptomyces lividans* which prevents intraplasmid recombination has no effect on chromosomal recombination" *Mol. Gen. Genet.*, vol. 220, pp. 60–64, 1989.

(List continued on next page.)

*Primary Examiner*—Robert A. Wax
*Assistant Examiner*—Rebecca Prouty
*Attorney, Agent, or Firm*—Lahive & Cockfield

[57] ABSTRACT

Cell lines useful for analysis of human homologous interchromosomal recombination are described. The cell lines carry endogenous mutant alleles of a selectable gene and can regenerate a selectable phenotype through homologous genetic recombination but not by large deletion of nucleotides or by chromosome loss. Assays using the cell lines permit quantitative and qualitative analysis of recombination events which occur between human chromosomes in somatic cells in culture. The assay relies on normal genes in their normal chromosomal site. The assays can be used to test for environmental agents which induce homologous recombination in human cells.

8 Claims, 7 Drawing Sheets

OTHER PUBLICATIONS

Kolodner, R. et al., "Genetic Recombination of Bacterial Plasmid DNA: Effect of RecF Pathway Mutations on Plasmid Recombination in *Escherichia coli*" *Journal of Bacteriology*, vol. 163, No. 3, pp. 1060–1066, Sept. 1985.

Liber, H. L. and W. G. Thilly, "Mutation assay at the thymidine kinase locus in diploid human lymphoblasts" *Mutation Research*, vol. 94, pp. 467–485, 1982.

Little, J. B. and M. B. Benjamin, "Molecular Structure Of Mutations At An Autosomal Locus In Human Cells: Evidence For Interallelic Homologous Recombination" *Annales de Génétique*, vol. 34, Nos. 3&4, pp. 161–166, 1991.

Orita, M. et al, "Detection of polymorphisms of human DNA by gel electrophoresis as single–strand conformation polymorphisms" *Proc. Natl. Acad. Sci. USA*, vol. 86, pp. 2766–2770, Apr. 1989.

Orita, M. et al., "Rapid and Sensitive Detection of Point Mutations and DNA Polymorphisms Using the Polymerase Chain Reaction" *Genomics*, vol. 5, pp. 874–879, 1988.

Potter, T. A. et al., "Mitotic recombination between homologous chromosomes generates H-2 somatic cell variants *in vitro*" *Proc. Natl. Acad. Sci. USA*, vol. 84, pp. 1634–1637, Mar. 1987.

Radman, M., "Mismatch repair and the fidelity of genetic recombination" *Genome*, vol. 31, pp. 68–73, 1989.

Rubnitz, J. and S. Subramani, "Rapis Assay for Extrachromosomal Homologous Recombination in Monkey Cells" *Molecular and Cellular Biology*, vol. 5, No. 3, pp. 529–537, Mar. 1985.

Tantravahi, U. et al., "Isolation of DNA sequences on human chromosome 21 by application of a recombination–based assay to DNA from flow–sorted chromosomes" *Hum. Genet.*, vol. 79, pp. 196–202, 1988.

Timme, T. L. et al., "Intermolecular Plasmid Recombination in Fibroblasts from Humans with DNA Damage–Processing Defects" *Plasmid*, vol. 22, pp. 1–9, 1989.

Turner, D. R. et al., "Mutations in human lymphocytes commonly involve gene duplication and resemble those seen in cancer cells" *Proc. Natl. Acad. Sci. USA*, vol. 85, pp. 3189–3192, May 1988.

Waldman, A. S. and R. M. Liskay, "Differential effects of base–pair mismatch on intrachromosomal versus extrachromosomal recombination in mouse cells" *Proc. Natl. Acad. Sci. USA*, vol. 84, pp. 5340–5344, Aug. 1987.

Wang, Y. et al., "Carcinogens Can Induce Homologous Recombination between Duplicated Chromosomal Sequences in Mouse L Cells" *Molecular and Cellular Biology*, vol. 8, No. 1, pp. 196–202, Jan. 1988.

Wasmuth, J. J. and L. V. Hall, "Genetic Demonstration of Mitotic Recombination in Cultured Chinese Hamster Cell Hybrids" *Cell*, vol. 36, pp. 697–707, Mar. 1984.

Amundson, S. A. et al., Nucleic Acids Research, vol. 19, No. 13, 11 Jul. 1991, p. 3748.

Little, J. B. and Benjamin, M. B., Annales De Genetique, vol. 34, No. 3–4, 28 Jan. 1992, pp. 161–166.

Benjamin, M. B. et al., Proceedings of the National Academy of Sciences of USA, vol. 88, No. 15, Aug. 1991, pp. 6652–6656.

Benjamin, M. B. and Little, J. B., Molecular and Cellular Biology, vol. 12, No. 6, Jun., 1992, p. 2730.

Groden et al. (1990) Proc. Natl. Acad. Sci. USA, 87:4315–4319.

Bhattacharyya et al. (1990) Mutation Research, 234:31–41.

Timme et al. (1989) Plasmid, 22:1–9.

Kieser et al. (1989) Mol. Gen. Genet, 200:60–64.

Orita et al. (1989) Genomics, 5:874–879.

Radman (1989) Genome, 31:68–73.

Orita et al. (1988) Proc. Natl. Acad. Sci. USA, 86:2766–2770.

Tantravachi et al. (1988) Human Genetics, 79:196–202.

Turner et al. (1988) Proc. Natl. Acad. Sci. USA, 85:3189–3192.

Wang et al. (1988) Molecular and Cellular Biology, 8: 1634–1637.

Potter et al. (1987) Proc. Natl. Acad. Sci. USA, 84:1634–1637.

Waldman et al. (1987) Proc. Natl. Acad. Sci. USA, 84:5340–5344.

Kolodner et al. (1985) Journal of Bacteriology, 163:1060–1066.

Rubintz et al. (1985) Molecular and Cellular Biology, 5:529–537.

Fishel et al. (1984) Journal of Bacteriology, 160:1168–1170.

Wasmuth et al. (1984) Cell, 36:697–707.

Cohen et al. (1983) Mol. Gen. Genet, 189:471–474.

Liber et al. (1982) Mutation Research, 94:467–485.

Ames et al. (1975) Mutation Research, 31:347–364.

E. A. Drobetsky et al. Mut. Res. 232:281–289 (Oct. 1990).

Y. Hidaka et al. J. Clin. Invest. 80:1409–1415 (Nov. 1987).

A. Sahota et al. Nuc. Acids Res. 18(19) 5915–5916 (Oct. 1990).

M. A. Ward et el. Carcinogenesis 11(9) 1485–1490 (Sep. 1990).

T. Chan et al. Somatic Cell Mol. Genet. 15(5) 411–420 (Sep. 1989).

A. L. Akenson et al. J. Biol. Chem. 263(31) 16291–16296 (Nov. 1988).

R. Hirschhorn et al. Proc. Natl. Acad. Sci. 87:6171–6175 (Aug. 1990).

Liber, H. L. et al. "Mutation Assay at the Thymidine Kinase Locus in Diploid Human Lymphobalasts" Mut. Res. 94:467–485 (1982).

Figure 4 tk-/- lines 6:86 & 6:97 revertant 6:86l revertant 6:97UC

CELL LINES AND METHODS FOR ASSAYING HUMAN INTERCHROMOSOMAL RECOMBINATION

This work was supported by one or more research grants from the United States government.

This application is a continuation of application Ser. No. 07/738,316, filed on Jul. 31, 1991, now abandoned.

BACKGROUND OF THE INVENTION

For the study of genetic toxicology, assays have traditionally been those which follow forward and reverse mutation. Forward mutagenesis assays are designed to test the ability of a mutagen to inactivate a given gene and generate a novel, selectable phenotype through DNA sequence alteration. The TK6 lymphoblast line (Liber, H. L. and Thilly, W. G. (1982) *Mutat. Res.* 94:467–485), which is heterozygous for the thymidine kinase (tk) gene and hemizygous for the X-linked hypoxanthine-guanine phosphoribosyl transferase (hprt) gene, is used as a human forward mutation assay. Cells can be exposed to a suspected mutagen and tk$^-$/ mutants selected for in trifluorothymidine ($F_3$TdR; if tk is used) or 6-thioguanine (6TG, if hprt is used).

Highly specific reverse mutation assays test the ability of an agent to reverse the effects of a defined mutation in a gene, thereby regenerating gene function and restoring a selectable phenotype. The Ames assay system, which employs specific Salmonella mutations, serves as such a reverse assay (Ames, B. N. et al. (1975) *Mutat. Res,.* 31:347–364). More recently, a third class of assay has been developed in mammalian cells. These assess the ability of agents to induce genetic recombination.

Cancers such as Wilm's Tumor (Koufos, A. et al. (1984) *Nature* 309:170–172; Orkin, S. H. et al, (1984) *Nature* 309:172–174; Dao, D. D. et al, (1987) *Am. J, Hum. Genet.* 41:202–217), retinoblastomas and osteosarcomas (Cavenee, W. K. et al. (1983) *Nature* 305:779–784; Dryja, T. P. et al. (1984) *N. Engl, J. Med.* 31.0:550–553; Hansen, M. F. et al, (1985) *Proc. Natl. Acad. Sci. USA* 82:6216–6220), astrocytomas (James, C. D. et al. (1989) Proc. Natl. Acad. Sci, USA 86:2858–2862), meningiomas and acoustic neuromas (Seizinger, B. R. et al, (1986) Nature 322:644–647; Okazaki, M. et al., (1988) *Mol. Biol. Med.* 5:15–22) are known to arise through a number of somatic events which include somatic recombination. The global loss of heterozygosity seen in progressing common tumors such as colorectal carcinomas (Vogelstein, B. et al., (1989) *Science* 244:207–211) may also be due to somatic recombination.

As evidence mounts for the role of somatic recombination in human tumors, this form of genetic alteration in human cells has attracted considerable interest. Two principal forms of recombination assay are currently in use: extrachromosomal assays (inter- and intra-molecular recombination); and, integrated assays (recombination between exogenous DNA integrated in the genome).

In extrachromosomal assays, recombination substrates are extrachromosomal plasmids existing as either single copy or multiple copy elements in the nucleus. Plasmids commonly carry two overlapping non-functional fragments of a single selectable marker or two copies of the gene which are inactivated by mutations at different sites. The bacterial neomycin phosphotransferase gene, which confers G418 resistance in mammalian cells, or the Herpes simplex virus (HSV) tk gene, conferring HAT resistance, are the most frequently used markers in these assays. Recombination between or within such plasmids can restore a functional gene and selectable phenotype.

However, data from prokaryotic studies indicate that extrachromosomal DNA is recombined and repaired by pathways which differ from those involved in chromosomal recombination. The rec-46 mutation in *Streptomyces lividans*, which prevents recombination between direct repeats in an extrachromosomal plasmid, does not affect the level of chromosomal recombination in these cells (Kieser, H. M. et al, (1989) *Mol. Gen. Genet.* 220:60–64). Similarly the *Escherichia coli* recA, recF, recO, and topA mutations all affect intraplasmid homologous recombination whilst only recA has any effect on chromosomal recombination events (see Cohen, A. and Laban, A. (1983) *Mol. Gen. Genet.* 189:471–474; Fishel, R. A. and Kolodner, R. (1984) *J. Bacteriol.* 160:1168–1170; Kolodner, R. et al. (1985) *J. Bacteriol.* 163:1060–1066).

In mouse cells (Waldman, A. S. and Liskay, R. M. (1987) *Proc. Natl. Acad. Sci. USA* 84:5340–5344), studies show that the DNA sequence heterologies existing between HSV type 1 and 2 tk genes will reduce homologous recombination between these genes relative to recombination between the perfectly homologous HSV type 1 tk genes. However, this reduction, is dramatic only when the substrates are integrated into the mouse genome (1000-fold). When the sequences are transfected into the cells as extrachromosomal molecules, they show only a 3–15 fold reduction in inter- and intramolecular recombination. It has therefore been suggested that mismatch repair enzymes may act preferentially upon chromosomal DNA as opposed to exogenous sequences (Radman, M. (1989) *Genome* 31:68–73).

Extrachromosomal DNA is also recombined at very high frequency. Following microinjection into mouse cells it has been estimated that injected molecules may undergo one recombination event each, only some of which generate an active gene (Folger, K. R. et al. (1985) *Mol. Cell. Biol.* :5.59–69), and in the same studies coinjected plasmid DNA was shown to become refractory to recombination if a gap of one hour elapsed between the injection of each plasmid component. These results imply that, unlike chromosomal sequences, plasmid DNAs are able to recombine at very high frequencies and that once recruited into chromatin, this recombination is dramatically attenuated.

In integrated assays, researchers have utilized foreign sequences integrated into the chromosomal DNA of the test cell. In some assays, the tandem arrangement of integrated HSV tk sequences allowed for the analysis of both reciprocal and non-reciprocal events. However, this assay was often complicated by an inability to distinguish between intrachromatid exchanges and sister-chromatid events (Wang, Y. et al. (1988) *Mol. Cell. Biol.* 8:196–202; Bhattacharyya, N. P. et al. (1990) *Mutation Research* 234:3141).

Integrated markers may also have inherent structural complications. The level of recombination in and around the site of an exogenous sequence integration site or a chromosomal translocation in mammalian cells may be permanently elevated (Murnane, J. P. and Young, B. R. (1989) *Gene* 84:201–205; Murnane, J. P. (1990) *BioEssays* 12:1–5). This might indicate that integration-induced instabilities are a factor in the recombination occurring between integrated tandem repeats.

The assay systems described above have permitted the dissection of recombination in mammalian cells but they are unlikely to serve as adequate models for interchromosomal recombination. Extrachromosomal sequences are not structurally restricted by chromatin and are free to associate in the nucleus. Endogenous, integrated tandem arrays place almost identical sequences side-by-side in the genome and permit recombination between them or between post S-phase sister chromatids. Neither of these two mechanisms resemble interchromosomal recombination in the mitotic nucleus where homologs are not associated and alleles of a given gene are not held in juxtaposition.

Chromosomal recombination has been studied in mammalian cells. Studies of interchromosomal homologous recombination in human cells have largely relied on gene dosage analysis after examination of spontaneously arising mutant clones in cell culture (Turner, D. R. et al, (1988) *Proc. Natl. Acad. Sci. USA* 85:3189–3192; Groden, J. et al, (1990) Proc. Natl. *Acad. Sci. USA* 87:4315–4319). The detection of allele loss, stretches of homozygosity and the generation of novel linkage relationships have also been described in rodent cell lines (Wasmuth, J. J. and Vock Hall, L. (1984) *Cell* 36:697–707; Potter, T. A. et al. (1987) *Proc. Natl. Acad, Sci, USA* 84:1634–1637). Although these assays allow for both a qualitative and quantitative analysis of such recombination events, they are unable to follow the recombination event at a particular gene. In many instances chromosomal loss and reduplication is the principal mechanism of change in these lines.

Improved systems for the assay of homologous interchromosomal recombination in human cells are needed.

SUMMARY OF THE INVENTION

This invention pertains to cell lines that can be used to assay homologous interchromosomal recombination. The assay can be used to study recombination at particular genes and to screen environmental agents for recombinogenic activity.

The cells of this invention have mutations in both alleles of a chromosomal gene resulting in the deactivation of the gene and the loss of a selectable phenotype. The phenotype can be restored by homologous interallelic recombination which regenerates at least one functional allele, but not by large deletions of nucleotides (of more than about 10 nucleotides) or by chromosome loss. In a preferred embodiment, the cells have a different frameshift mutation in each allele of the gene which provides the selectable phenotype. A preferred gene is the thymidine kinase gene. Cells carrying different frameshift mutations in each allele of the thymidine kinase gene are CHAT sensitive (tk⁻) and can revert to the CHAT resistant (tk⁺) phenotype by interallelic recombination.

To assay for the recombinogenic activity of an agent, a cell line of this invention is exposed to the agent. If necessary, the cells are allowed to recover from the toxic effects of exposure. The exposed cells are then selected for reversion to the selectable phenotype. The frequency of reversion to the selectable phenotype among the exposed cells is compared to controls (unexposed cells and/or cells which are unable to revert to the selectable phenotype by interallelic recombination). An increase in the frequency of reversion of exposed cells indicates that the agent has recombinogenic activity. The chromosomal DNA (or a portion thereof) of the exposed cells can be analyzed to determine the actual frequency of interallelic recombination and the recombinogenic activity of the agent.

The assay of this invention permits the detailed quantitative and qualitative analysis of recombination events which occur between human chromosomes in somatic cells in culture. It relies on normal genes in their normal chromosomal site. The assay provides sensitive tests for environmental agents which induce homologous recombination in human cells.

DETAILED DESCRIPTION OF THE INVENTION

The cell lines of this invention have mutations in both alleles of a chromosomal gene which provides a selectable phenotype. The mutations deactivate the gene, thereby causing loss of the phenotype. The mutations are such that the cells can revert to the selectable phenotype by homologous interallelic recombination, but not by large deletions of nucleotides (generally of more than 10 nucleotides) or by chromosome loss.

The mutations can be made in any autosomal gene which provides a selectable phenotype. Examples of genes which provide a selectable phenotype and are suitable for mutation are the genes encoding thymidine kinase and adenine phosphoribosyl transferase.

In a preferred embodiment, the cell lines carry different frameshift mutations at both endogenous alleles of the gene. The frameshift mutations comprise an addition or deletion of an appropriate number of nucleotides at an exon. Frameshift mutations at different locations in alleles of a gene allow restoration of function by a limited number of mechanisms, namely, some frame-restoring nucleotide additions and deletions, gene conversion and recombination. The cell lines should revert to phenotype at a low spontaneous frequency (for example, $10^{31\ 7}$ to $10^{-8}$) to allow sensitive detection of recombination activity.

In particularly preferred embodiments, the cell lines carry different frameshift mutations at each allele of the gene encoding thymidine kinase. These cells exhibit the tk⁻ phenotype and are therefore sensitive to CHAT medium (cytidine, hypoxanthine, aminopterin and thymidine). Recombination between the human thymidine kinase alleles on chromosome 17, which can occur by the mechanisms mentioned above, regenerates the tk⁺ phenotype which can be selected in culture.

Especially preferred cell lines are the cell lines 6:86 and 6:97 (believed to independent isolates of a single mutant clone generated by mutagenesis with ICR-191, as described more fully below). The cell lines are tk⁻ and have heterozygous mutations in the thymidine kinase gene (one in exon 4 of one allele and one in exon 7 of the other allele). Spontaneous reversion to tk⁺ phenotype occurs at a low frequency (approximately $10^{-7}$ –$10^{-8}$). Allelic maps of the maternal and paternal chromosome 17s in the lines used allow for detailed analyses of recombination events which lead to phenotypic reversion in culture.

In another embodiment, the mutations can be small deletions (preferably 5–10 nucleotides) located in different non-overlapping positions in each allele. These mutations can be formed by targeted insertion of oligonucleotides containing the deletions.

The cell lines of this invention can be prepared from any mammalian cells capable of being grown in culture. Examples are lymphocytic and fibroblastic cells. For analysis of the recombinogenic activity of an agent in humans, human cell lines are preferred. Preferred human cells are lymphocytic, particularly lymphoblastic cells.

Standard techniques of mutagenesis or gene targeting can be used to generate the appropriate mutations. Frameshift mutations are preferably achieved by mutagenesis with the alkylating nitrogen mustard ICR-191. ICR-191 is a potent frameshift mutagen, causing almost exclusively +1 or −1 frameshifts in *Salmonella* and *E. Coli* and can be used to induce such mutations in human cells.

The cell lines can be used in assays to screen environmental agents for recombinogenic activity in human cells. The agents can be chemicals such as drugs, toxins, food additives, and industrial reagents or pollutants. The agent can also be ionizing or non-ionizing radiation.

The cells are exposed in culture to the agent to be tested. Soluble chemical agents can be dissolved into the cell culture medium. Ionizing or non-ionizing irradiation can be performed by standard procedures.

The cells are exposed to predetermined concentrations of agent for a predetermined period of time. The concentration and time of exposure are typically determined by prior toxicity analysis according to standard procedure.

After exposure, the agent is removed from the cell culture. The cells can be centrifuged out of suspension in the medium containing a chemical agent, washed and then resuspended in fresh medium. Of course, separation is unnecessary when cells are irradiated. If necessary, the cells are allowed to recover from the toxic effects of exposure to the agent. Three days are routinely allowed for complete recovery from exposures prior to the selection step.

Exposed cells are selected for reversion to the selectable phenotype. To select for reversion to the $tk^+$ phenotype (CHAT resistance), exposed cells are cultured in a CHAT medium. CHAT medium contains cytidine, hypoxanthine, aminopterin and thymidine and blocks de novo purine synthesis. Only $tk^+$ cells which can rely on the salvage pathway for purine synthesis grow in this medium.

The selection step yields the frequency of reversion to the selectable phenotype among the exposed cells. The frequency of reversion is compared to that obtained for controls. Controls normally include unexposed cells which indicate the frequency of spontaneous reversion. Control cells should also include cells exposed to the agent but which are unable to revert to the selectable phenotype by interallelic recombination. For example, the cell line 4:2 (described below) is homozygous for a frameshift mutation in the thymidine kinase gene and is not expected to revert to the $tk^+$ phenotype by homologous interallelic recombination.

A greater frequency of reversion of exposed cells over both types of controls indicates that the agent has recombinogenic activity. The chromosomal DNA (or a portion thereof) of the exposed cells can be analyzed to determine the actual frequency of interallelic recombination and the recombinogenic activity of the agent. Allele loss as determined by restriction fragment length polymorphism (RFLP) analysis or the retention of both frameshifts in revertant cells as determined by single strand confirmation polymorphism (SSCP) analysis coupled with the presence of wild type message (mRNA) indicate that reversion has occurred by reciprocal combination.

The invention is illustrated further by the following exemplification:

EXEMPLIFICATION

Construction Of Cell Line

A phenotypically $tk^-$ cell line ($F_3TdR$ resistant) has been developed from the $tk^+$ line WIL-2 (NS) obtained from the ATCC (catalog #CRL-8155). This phenotypic alteration was achieved through several rounds of mutagenesis using the well-characterized alkylating nitrogen mustard ICR-191 (Polysciences Incorp., Warrington, Pa.). As mentioned, ICR-191 is a potent frameshift mutagen, causing almost exclusively +1 or −1 frameshifts in *Salmonella* and *E. coli* (Oeschger, N. S. and Hartman, P. E. (1970) *J. Bact.* 101:490–504; Calos, M. P. and Miller, J. H. (1981) *J. Mol. Biol.* 153:39–66; Stankowski, L. F., Jr. et al. (1986) *Mutation Research* 160:133–147).

400 mls of WIL-2 cells at a density of approximately $2 \times 10^5$/ml ($8 \times 10^7$ cells) were incubated with 0.45 mg/ml ICR-191 in complete medium with fetal calf serum for 4 hrs. The cells were then resuspended in fresh medium and allowed to recover for 5 to 6 days prior to any further exposure. After each round of ICR-191 treatment, $tk^-$ mutants were selected by plating approximately $4 \times 10^8$ cells in microtiter wells with 2 mg/ml of $F_3TdR$. $F_3TdR$ resistant ($F_3TdR^r$) clones arose after approximately 11 days of selection at which time they were picked and expanded for analysis.

Characterization of tk- Lines $F_3TdR^r$ lines were characterized at the DNA level by exon-specific polymerase chain reaction (PCR) amplification (Saiki, R. K. et al. (1988) *Science* 239:487–491) and direct dideoxy chain termination sequencing (Sanger, F. et al. (1977) *Proc. Natl. Acad. Sci. USA* 74:5463–5467). Based on the known tk genomic sequence (Flemington, E. et al. (1987) *Gene* 52:267–277) 19–22 base oligonucleotide primers were synthesized using a Pharmacia "Gene Assembler" (Pharmacia LKB Biotechnology Inc., Piscataway, N.J.) and were employed as primers for PCR in which cell line genomic DNA served as a template. This technology was applied to the characterization of lines 6:86 and 6:97, both isolated following six rounds of ICR-191 mutagenesis, and line 4:2 isolated after round four. Sequencing of PCR products allowed for the localization of deleterious mutations in these lines. The lines 6:86 and 6:97 appear to be independent isolates of a single mutant clone.

Mutations

The sequences shown below are from the anti-sense DNA strand and the inserted base is underlined. Both mutations are +1 frameshifts caused by the addition of a single GC base-pair. In each case the mutation is heterozygous and readily detected on sequencing gels. These are the only mutations detected in $tk^-/^-$ lines 6:86 and 6:97.

Exon 4. Bases 4850-51:

GAACACCATGGAGGCG (Seq ID No: 1) mutated to GAACACCATGGAGGCG (Seq ID No: 2). Based on the tk genomic sequence, this extra base is predicted to have no effect on transcription but will lead to the incorporation of 31 incorrect amino acid residues during translation and premature termination at residue 103.

Exon 7. Bases 12519-23:

GGTGATTGGGGGAGCAG (Seq ID NO:3) mutated to GGTGATTGGGGGAGCAG (Seq ID NO:4). This extra base is predicted to lead to the incorporation of 37 incorrect residues and the extension of tk protein by 131 additional amino acids (representing a 56% increase in tk monomer length).

Karyotype Analysis

Lines 4:2, 6:86, and 6:97 each have two normal appearing chromosome 17s.

Figure 1:
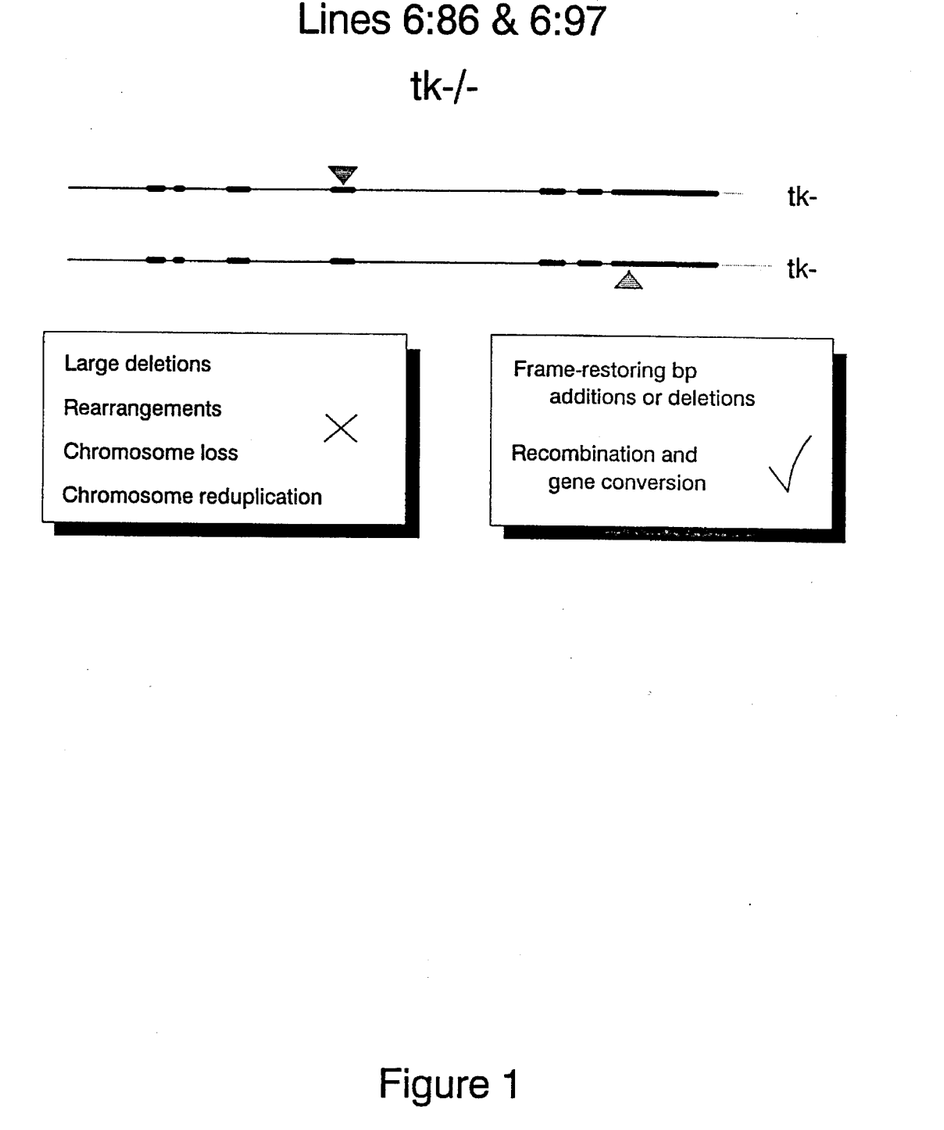
FIG. 1 shows schematically the exon location of the heterozygous mutations in alleles of the thymidine kinase gene in cell lines 6:86 and 6:97.

Since both mutations are heterozygous and the lines are apparently not expressing tk protein, these data support a single mutation in each allele; one allele carrying a mutation in exon 4, the other in exon 7 (FIG. 1). Work involving single-strand conformation polymorphisms (see below) has allowed line 4:2 to be characterized as a homozygote for the exon 7 mutation described above.

Restriction Fragment Length Polymorphisms (RFLP):

Four chromosome 17-linked probes were employed in this assay system. The four informative (heterozygous) probes are:

pTKl1: A full length cDNA probe for the TK1 gene. Reveals a SacI RFLP (Bradshaw H. D., Jr. and Deininger, P. L. (1984) *Mol. Cell Biol.* 4:2316–2320) with alleles at 14.8 and 8.4kb in WIL-2, 6:86 and 6:97.

pC63: An anonymous probe for the D17S21 locus proximal to tk. Reveals an MSpI RFLP (Kondoleon, S. et. al. (1987) *Nucleic. Acids. Res.* 15:9096–9096) with alleles at 4.3 and 3.9kb in WIL-2, 6:86 and 6:97.

pTHH59: An anonymous probe for D17S4 proximal to tk. Reveals a TaqI RFLP (Kidd, K. K. et al. (1989) *Cytogen. Cell Genet.* 51:622-947 and references cited therein) with alleles at 3.0 and 2.7kb in WIL-2, 6:86 and 6:97.

pRMU3: A sub-telomeric probe for the D17S24 locus distal to tk on 17q. Reveals a TaqI RFLP (Myers, R. et al. (1988) *Nuc. Acids. Res.* 16784-784; Nakamura, Y. et al. (1988) *Genomics* Z:302–309) with alleles at 3.0 and 2.7kb in WIL-2, 6:86 and 6:97.

Figure 2:
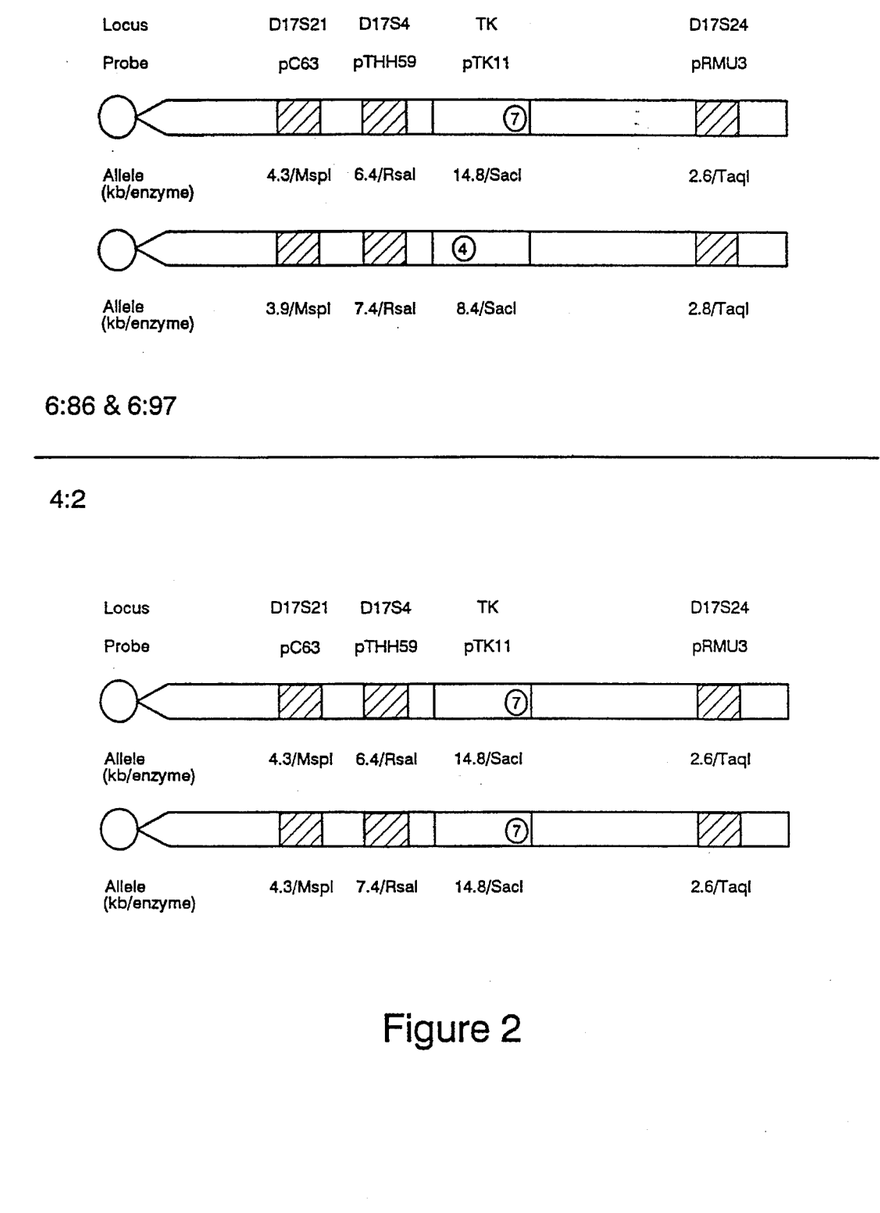
FIG. 2 are allelic maps of the chromosome 17s in the cell lines 6:86 and 6:97 as well as 4:2.

The homozygote 4:2 has enabled the construction of allelic maps of the chromosome 17s present in the 6:86 and 6:97 lines (FIG. 2). These add significant detail to the recombination assay.

Assay System

Figure 3:
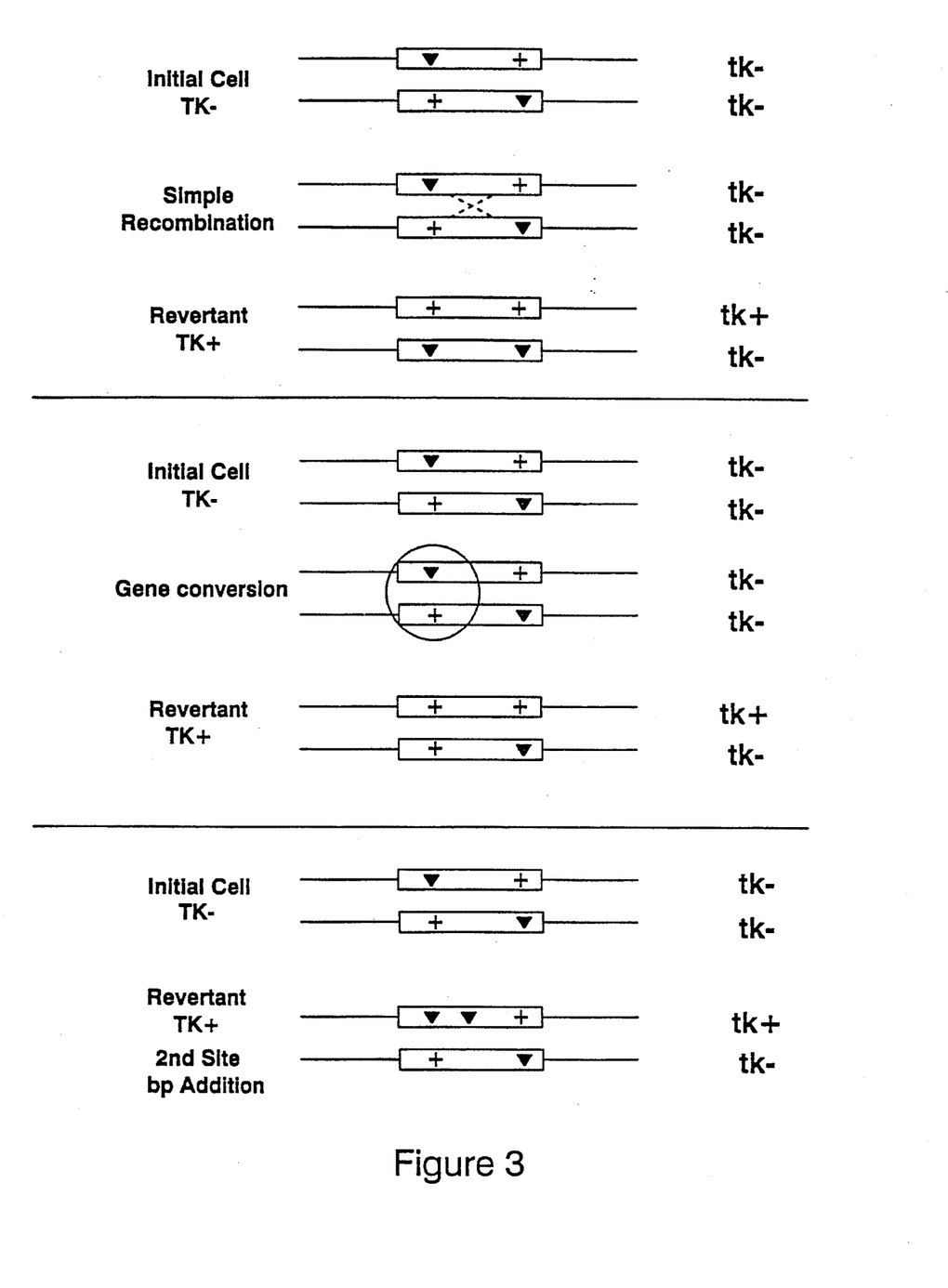
FIG. 3 illustrates the mechanisms by which reversion to a tk⁺ phenotype can occur in the cell lines 6:86 and 6:97.

The location of mutations in the 6:86 and 6:97 cell lines render these lines $tk^{-/-}$. Reversion to $tk^{+/-}$ or $tk^{-/+}$ can occur by only a limited number of mechanisms such as some base-pair deletions and additions, gene-conversions, or recombination (FIG. 3). Large deletions, rearrangements, translocations, chromosome loss, or loss and reduplication are not expected to yield $tk^+$ alleles. The assay involves exposing the cells to potential recombinogens, allowing the cells to recover from any toxic effects of this exposure and then plating them under selective conditions in order to isolate $tk^+$ revertants.

Exposure

Figure 4:
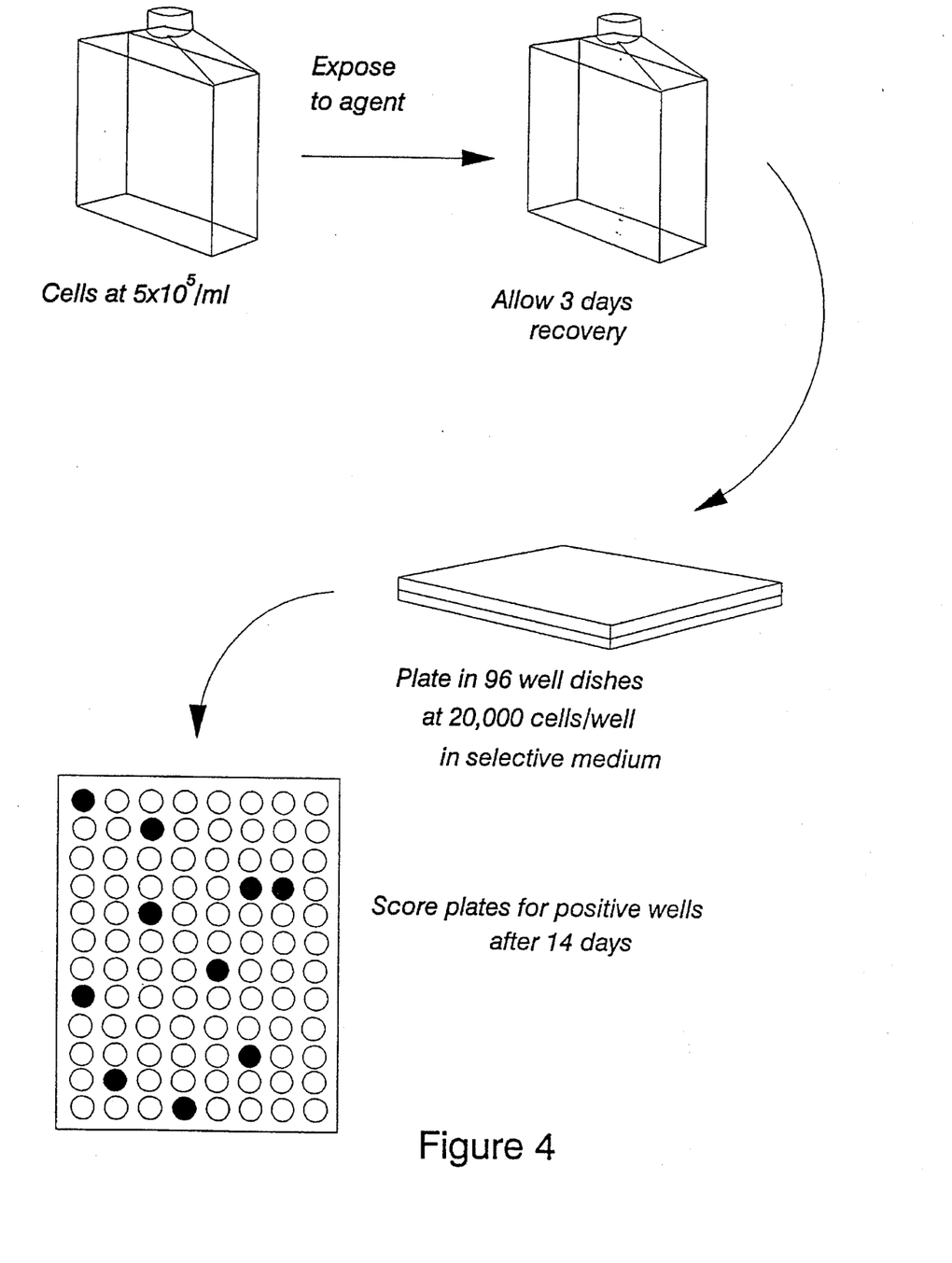
FIG. 4 shows the steps of an embodiment of the assay of this invention.

Lines 4:2, 6:86 and 6:97 grow in suspension in RPMI 1640 medium supplemented with 10% fetal calf serum and can therefore be readily exposed to genotoxins in solution. 200 ml of cells at $5\times10^5$ cells/ml ($10^8$ cells) are exposed in suspension to a potential recombinogen over a period of time determined by prior toxicity analysis. Examples are 0.45 mg/ml of ICR-191 for 4 hours or 0.1 µM Mitomycin C for 22 hours. Exposure to ionizing radiation such as x-rays has involved direct acute exposure of cultures to doses ranging from 50 to 200 cGy (Rads). After exposure to a chemical agent, cells are centrifuged out of suspension and resuspended in fresh, prewarmed medium. This is unnecessary when using irradiation. Three days are routinely allowed for complete recovery from exposures prior to plating in selective agent (FIG. 4).

2. Selection:

Medium is supplemented with 15% fetal calf serum and CHAT to select for $tk^+$ revertants from the 4:2, 6:86, 6:97 $tk^{-/-}$ mutants. Revertants which become $tk^+$ and express a tk allele are able to survive and form colonies in CHAT medium. After plating cells at 20,000/well ($10^5$/ml) in CHAT, resistant colonies can be scored and isolated on day 14 (FIG. 4).

Analysis

Colonies are picked into 3mls of medium and expanded to 50–200 mls of dense culture ($5-10\times10^5$/ml) before DNA is isolated. Genomic DNA is isolated by any standard procedure for isolation from lymphoblast cells. Revertant cell DNA and mRNA are then analyzed in three steps:

i. DNA RFLP analysis Through standard digestion, blotting and hybridization, (Maniatis, T., Fritsch, E. F., and Sambrook, J., *Molecular Cloning: A Laboratory Manual*, Cold Spring Harbor, Cold Spring Harbor Laboratory, 1982) Southern blots of genomic DNA are generated for each revertant.

TABLE 1

Genetic Constitution of Cell Line Chromosome 17s

| Probe | Locus | Location | Enzyme | Allele, kb Lines 6:86 and 6:97 | Line 4:2 |
|---|---|---|---|---|---|
| C63 | D17S21 | 17q23-qter | MspI | 3.9, 4.3 | 4.3 |
| THH59 | D17S4 | 17q23-2S.3 | RsaI | 7.4, 6.4 | 6.4 |
| TKII | TK | 17q23.2-2S.2 | SacI | 8.4, 14.8 | 14.8 |
| RMU3 | D17S24 | 17q (distal) | TaqI | 2.8, 2.6 | 2.6 |
| Frame-shifted TK exons | | | | 4 and 7 | 7 | kb, Kilobases

Revertants which have arisen through point mutations within the TK gene, i.e., second site mutations which restore the reading frame or mutations which remove the additional base, are not expected to show changes at any linked markers. Screening for changes at linked markers is therefore routine in revertants. Changes at the SACI RFLP revealed by pTKl1 have been seen in both a spontaneous revertant and a revertant which may have been induced with ICR-191. Neither of these revertants is expected to show RFLP changes and both are believed to be recombinants (see below). Markers distributed throughout human chromosome 17 are now available, both proximal and distal to tk.

Results

Figure 5:
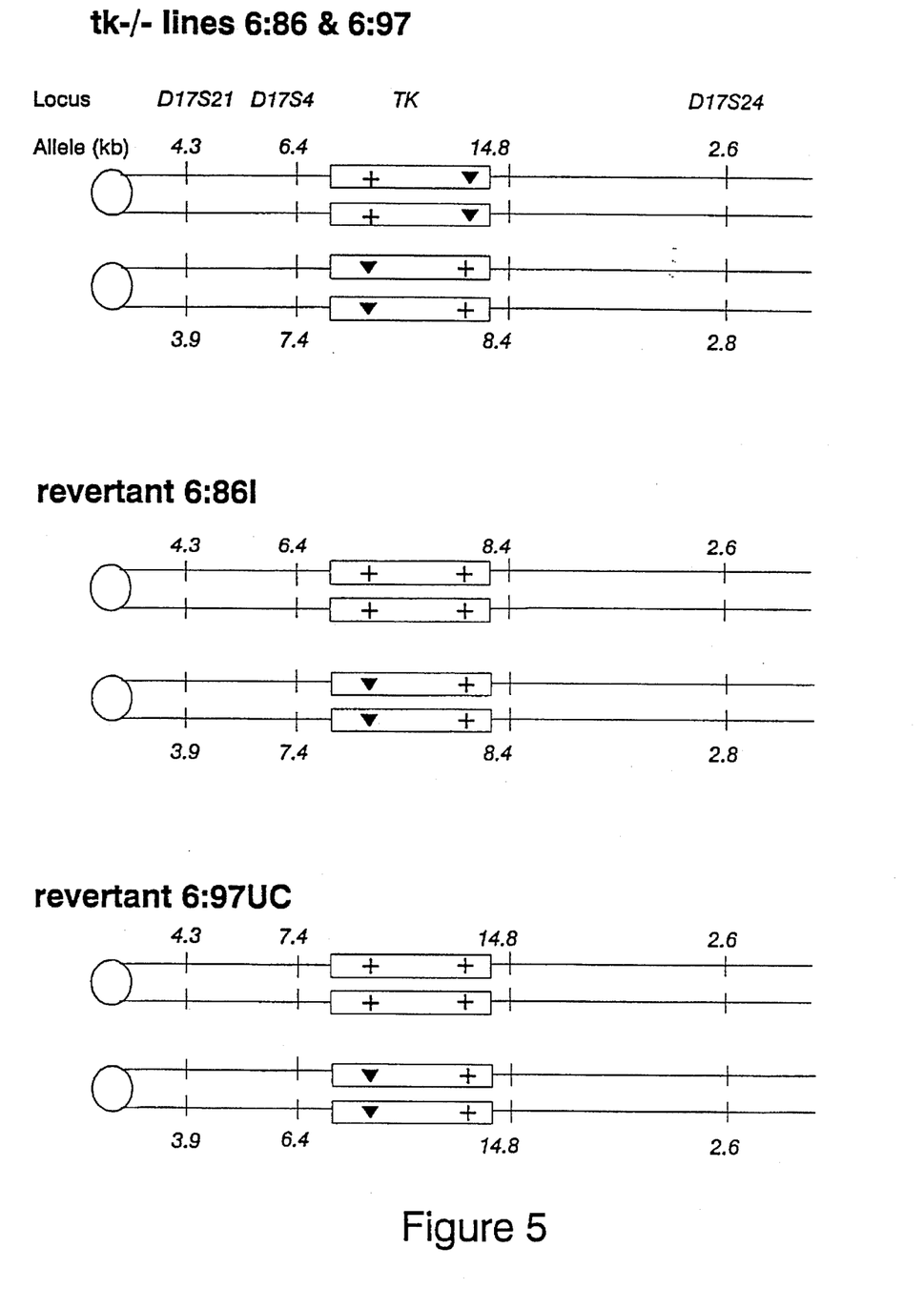
FIG. 5 shows the genotype of two revertants (6:86I and 6:86UC) that arose from line 6:86 by recombination.

Of 63 revertants examined to date (both spontaneous and induced) 2 have shown clear RFLP changes on chromosome 17. 6:86I, a 6:86 revertant exposed to ICR-191, shows reduction to homozygosity at the 8.4 kb SacI allele for pTKll but remains heterozygous for the proximal pTHH59 and distal pRMU3 RFLPs and the proximal pC63 RFLP. 6:97UC, which is a spontaneous revertant from 6:97 is now homozygous for the 14.8 kb SacI allele at pTKll and the distal 2.6kb TaqI allele at pRMU3. It remains heterozygous at all other markers including pTHH59 (FIG. 5).

ii. DNA Single-Strand Conformation Polymorphisms

This technique (Orita, M. et al. (1989) *Genomics* 5:874–879; Orita, M. et al. (1989) *Proc. Natl. Acad. Sci. USA* 86:2766–2770) allows for the rapid characterization of revertants to $tk^+$ at the DNA level. Single strand conformation polymorphisms (SSCPs) represent the differential migration of single stranded DNA in a non-denaturing polyacrylamide gel as a function of DNA sequence. High molecular weight DNA is prepared from revertant lines and utilized as a template in PCR amplification. PCR reactions include $^{32}P$-$\alpha$dCTP (3000 Ci/mmol, New England Nuclear) which is incorporated during amplification. Labelled PCR products are then mixed with SSCP buffer and heat denatured. The single stranded PCR products are loaded onto a non-denaturing polyacrylamide gel (64 polyacrylamide, 0 3% bis, lot Glycerol and no Urea) and run at 30W constant power at room temperature or 4° C. for 6 hours (see below). Gels are dried as usual and autoradiography is performed for 3–6 hours at −80° C. in the presence of an intensifying screen. SSPC oligonucleotide primers S1 (Seq ID No. 5) (5'CACGCTCTGGCTTTCTCTTC 3') and S2 (Seq ID No. 6) (5'ATGCCAAGACAAGCCAACTT 3') were synthesized in order to amplify exon 4 of the tk gene; primers S3 (Seq ID No: 7) (5'TCCTTCCTGTCCTGGCCCTT 3') and S4 (Seq ID No: 8) (5'CAGTTCTCTTTGTTGTCCGG 3') for the amplification of the upstream end of exon 7. SSCP analysis of exon 4 PCR-products run in non-denaturing gels at 4° C. reveals 2 dense bands from WIL-2 and 4 lighter bands with the DNA from 6:86 or 6:97. All three of these lines carry the two wild type bands but 6:86 and 6:97 carry two additional (mutant) bands. For exon 7 analysis, band resolution was maximized by running the gel at room temperature.

Figure 7:
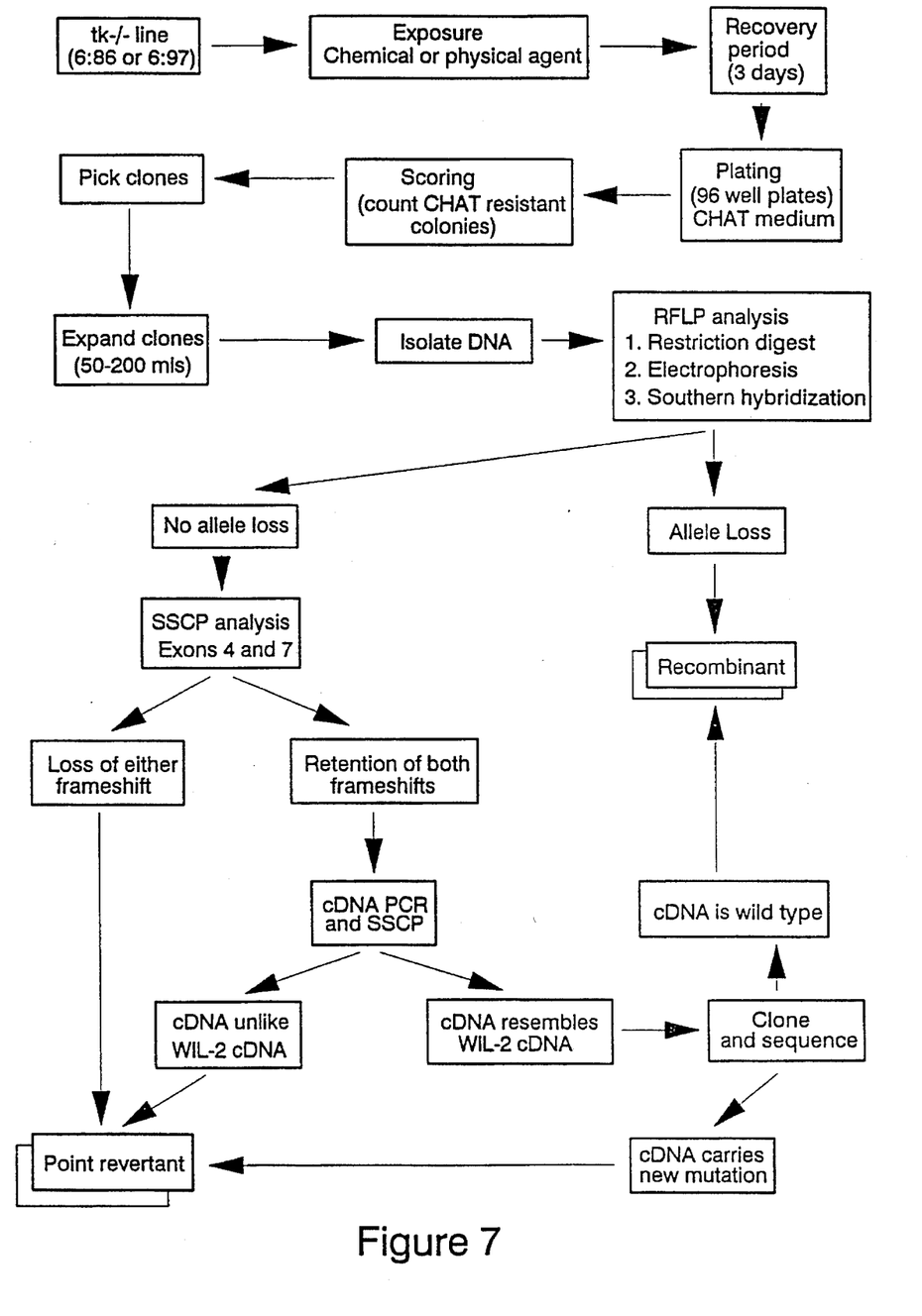
FIG. 7 outlines the analysis of revertant (tk⁺) cell DNA.

To date 41 $tk^+$ revertants have been analyzed by PCR-SSCP. Through this analysis the revertants can be divided into three groups:

1. Become $tk^+$ by restoring a wild type sequence at a frameshift site;

2. Become $tk^+$ by restoring the reading frame with a second site mutation; and 3. Become $tk^+$ but retain both frameshifts with no additional mutation found. Revertants which fall into groups 1 or 2 are classified as point-revertants (reverting by a compensating mutation). Those in group 3 are classified as potential recombinants (FIG. 7).

iii. mRNA Single-Strand Conformation Polymorphisms

Figure 6:
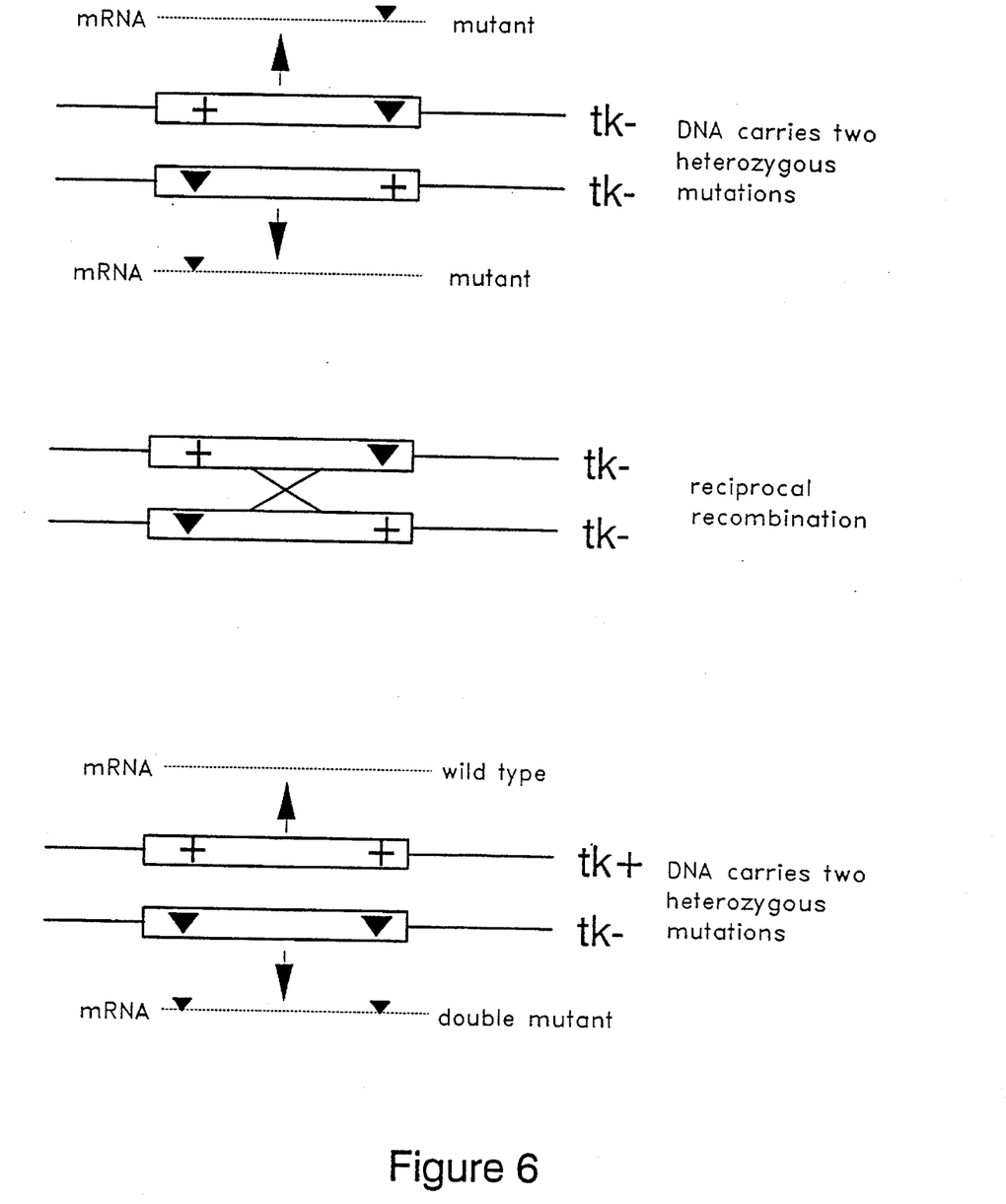
FIG. 6 shows how wild type mRNA is generated following reciprocal recombination in line 6:86.

Reconstruction of a $tk^+$ gene by reciprocal recombination in the 8 kb between the exon 4 and 7 mutations is expected to produce a wild type allele and a double-mutant allele. A single reciprocal recombination between the two tk− alleles in 6:86 or 6:97 which generates a functional $tk^+$ allele will consequently lead to the synthesis of two forms of mRNA: a wild type message, and a double mutant message (FIG. 6). The identification of such wild type or double-mutant mRNA in any of the $tk^+$ revertants known to retain both exon 4 and exon 7 mutations will therefore be proof of a reciprocal recombination event.

A cell pellet of $10^6$ cells is washed in EBSS and incubated for 90 minutes at 37° C. in lysis/reverse transcriptase buffer (NP40, Tris, KCl, RNasin, $MgCl_2$, DTT, dNTPs, MU-MLV reverse transcriptase and buffer) with a specific tk mRNA oligonucleotide primer (M4). (Seq ID No: 10). This reaction then serves as template for PCR amplification using primers M3 (Seq ID No. 9) (5'ACAGAGTTGATGAGACGCGT) and M4 (Seq ID No: 10) (5'TTCCCCTGGCTTTCCTGGCA 3'). PCR product after this initial reaction is expected to be 540bp but is at too low a concentration to detect in agarose gels. The use of a second round of PCR amplification with nested primers M1 (Seq ID No. 11) (5'ATGAGTCGACACACATGACCGGAA 3') and M2 (Seq ID No: 12) (5'AAGTGTCGACGGAGTGGTACTTGT 3') produce a clearly visible fragment of 370 bp. Primers M1 (Seq ID No: 11) and M2 (Seq ID No: 12) contain SalI restriction sites (underlined) to enable subsequent cloning of PCR products for sequencing. This PCR product, which represents cDNA covering exons 4 to 7, is analyzed in two steps.

1. SSCP Analysis

Two cDNAs are expected from each revertant line which has undergone reciprocal recombination and retains both mutations.

One cDNA wild type and one the double-mutant. By comparison to WIL-2 cDNA (which will be wild type only) and 6:97 and 6:86 (which will produce two cDNAs carrying different mutations), wild type cDNA produced from a revertant can be rapidly screened for.

2. Sequencing

Confirmation of SSCP data is obtained by sequencing the PCR products. Restriction sites in primers M1 (Seq ID No: 11) and M2 (above) allow for a mixture of cDNAs (expected from a recombinant) to be independently subcloned into Bluescript KS and sequenced. The presence of either wild type or double-mutant cDNA is proof of reciprocal recombination (FIG. 7).

Cell Deposit

Human lymphoblastic cell line 6:86 was deposited at the American Type Tisse Culture Collection in Rockville, Md. on Jul. 30, 1992. The accession number is CRL 11090.

Equivalents

Those skilled in the art will recognize, or be able to ascertain using no more than routine experimentation, numerous equivalents to the specific procedures described herein. Such equivalents are considered to be within the scope of this invention and are covered by the following claims.

We claim:

1. A human cell line which has a different mutation in each allele of the endogenous thymidine kinase gene resulting in the loss of a selectable phenotype and which can revert to the phenotype by homologous interallelic recombination but not by large deletions of nucleotides or by chromosome loss.

2. The human cell line of claim 1, which is a human lymphoblastic cell line.

3. The human cell line of claim 1, wherein each allele of the thymidine kinase gene has a different frameshift mutation.

4. The human cell line of claim 3, wherein the frameshift mutations are the result of an insertion of a single nucleotide in each allele.

5. The human lymphoblastic cell line 6:86 (ATCC Accession No.: CRL 11090) having frameshift mutations in each of a first and second allele of a thymidine kinase gene, wherein in one allele the exon 4 sequence GAACACCATG-GAGGCG (SEQ ID NO:1) is mutated to GAACAC-CCATGGAGGCG (SEQ ID NO:2) and in the other allele the exon 7 sequence GGTGATTGGGGGAGCAG (SEQ ID NO:3) is mutated to GGTGATTGGGGGGAGCAG (SEQ ID NO:4).

6. The human cell line of claim 3, wherein the frameshift mutations are the result of a deletion of a single nucleotide in each allele.

7. The human cell line of claim 3, wherein the frameshift mutations are the result of deletions of multiple nucleotides in each allele.

8. The human cell line of claim 3, wherein the frameshift mutations are the result of insertions of multiple nucleotides in each allele.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear    ( i i ) MOLECULE TYPE: DNA    ( i i i ) HYPOTHETICAL: no    ( i v ) ANTI-SENSE: yes    ( v i i ) IMMEDIATE SOURCE: WIL-2 (NS) tk$^-$, F3TdR
      resistant cell line    ( v i i i ) FEATURE:
      ( A ) NAME/KEY: Exon 4, bases 4850- 51

( x i ) SEQUENCE DESCRIPTION: SEQ ID NO:1:

GAACACCATG GAGGCG                                      16

( 2 ) INFORMATION FOR SEQ ID NO:2:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear    ( i i ) MOLECULE TYPE: DNA    ( i i i ) HYPOTHETICAL: no    ( i v ) ANTI-SENSE: yes    ( v i i ) IMMEDIATE SOURCE: WIL-2 (NS) tk$^-$, F3TdR
      resistant cell line    ( v i i i ) FEATURE:
      ( A ) NAME/KEY: Exon 4, bases 4850- 51

( x i ) SEQUENCE DESCRIPTION: SEQ ID NO:2:

GAACACCCAT GGAGGCG                                    17

( 2 ) INFORMATION FOR SEQ ID NO:3:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear    ( i i ) MOLECULE TYPE: DNA    ( i i i ) HYPOTHETICAL: no    ( i v ) ANTI-SENSE: yes    ( v i i ) IMMEDIATE SOURCE: WIL-2 (NS) tk$^-$, F3TdR
      resistant cell line    ( v i i i ) FEATURE:
      ( A ) NAME/KEY: Exon 7, bases 12519- 23

( x i ) SEQUENCE DESCRIPTION: SEQ ID NO:3:

GGTGATTGGG GGAGCAG                                                                                      17

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: DNA     ( i i i ) HYPOTHETICAL: no     ( i v ) ANTI-SENSE: yes     ( v i i ) IMMEDIATE SOURCE: WIL-2 (NS) tk⁻, F3TdR
        resistant cell line     ( v i i i ) FEATURE:
        ( A ) NAME/KEY: Exon 7, bases 12519- 23

( x i ) SEQUENCE DESCRIPTION: SEQ ID NO:4:

GGTGATTGGG GGGAGCAG                                                                                     18

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA     ( i i i ) HYPOTHETICAL: no     ( i v ) ANTI-SENSE: yes     ( v i i ) IMMEDIATE SOURCE: biochemically synthesized     ( v i i i ) FEATURE:
        ( A ) NAME/KEY: oligonucleotide primer S1

( x i ) SEQUENCE DESCRIPTION: SEQ ID NO:5:

CACGCTCTGG CTTTCTCTTC                                                                                   20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA     ( i i i ) HYPOTHETICAL: no     ( i v ) ANTI-SENSE: yes     ( v i i ) IMMEDIATE SOURCE: biochemically synthesized     ( v i i i ) FEATURE:
        ( A ) NAME/KEY: oligonucleotide primer S2

( x i ) SEQUENCE DESCRIPTION: SEQ ID NO:6:

ATGCCAAGAC AAGCCAACTT                                                                                   20

( 2 ) INFORMATION FOR SEQ ID NO:7:

( i ) SEQUENCE CHARACTERISTICS:
        ( A ) LENGTH: 20 base pairs (B) TYPE: nucleic acid
(C) STRANDEDNESS: single
(D) TOPOLOGY: linear (i i) MOLECULE TYPE: DNA (i i i) HYPOTHETICAL: no (i v) ANTI-SENSE: yes (v i i) IMMEDIATE SOURCE: biochemically synthesized (v i i i) FEATURE:
(A) NAME/KEY: oligonucleotide primer S4

(x i) SEQUENCE DESCRIPTION: SEQ ID NO:7:

TCCTTCCTGT CCTGGCCCTT                 20

(2) INFORMATION FOR SEQ ID NO:8:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (i i i) HYPOTHETICAL: no (i v) ANTI-SENSE: yes (v i i) IMMEDIATE SOURCE: biochemically synthesized (v i i i) FEATURE:
(A) NAME/KEY: oligonucleotide primer M3

(x i) SEQUENCE DESCRIPTION: SEQ ID NO:8:

CAGTTCTCTT TGTTGTCCGG                 20

(2) INFORMATION FOR SEQ ID NO:9:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (i i i) HYPOTHETICAL: no (i v) ANTI-SENSE: yes (v i i) IMMEDIATE SOURCE: biochemically synthesized (v i i i) FEATURE:
(A) NAME/KEY: oligonucleotide primer M4

(x i) SEQUENCE DESCRIPTION: SEQ ID NO:9:

ACAGAGTTGA TGAGACGCGT                 20

(2) INFORMATION FOR SEQ ID NO:10:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (i i i) HYPOTHETICAL: no (i v) ANTI-SENSE: yes (v i i) IMMEDIATE SOURCE: biochemically synthesized (v i i i) FEATURE:
    (A) NAME/KEY: oligonucleotide primer M4

(x i) SEQUENCE DESCRIPTION: SEQ ID NO:10:

TTCCCTGGC TTTCCTGGCA                    20

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (i i i) HYPOTHETICAL: no (i v) ANTI-SENSE: yes (v i i) IMMEDIATE SOURCE: biochemically synthesized
        (A) LIBRARY: oligonucleotide primer M1

(x i) SEQUENCE DESCRIPTION: SEQ ID NO:11:

ATGAGTCGAC ACACATGACC GGAA              24

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (i i i) HYPOTHETICAL: no (i v) ANTI-SENSE: yes (v i i) IMMEDIATE SOURCE: biochemically synthesized (v i i i) FEATURE:
        (A) NAME/KEY: oligonucleotide primer M2

(x i) SEQUENCE DESCRIPTION: SEQ ID NO:12:

AAGTGTCGAC GGAGTGGTAC TTGT              24